US00PP37147P2

(12) United States Plant Patent
Bennett

(10) Patent No.: US PP37,147 P2
(45) Date of Patent: Dec. 16, 2025

(54) SHRUB ROSE PLANT NAMED 'AUSCP18729'

(50) Latin Name: *Rosa hybrida*
Varietal Denomination: AUSCP18729

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 19/049,975

(22) Filed: Feb. 10, 2025

(51) Int. Cl.
*A01H 5/02* (2018.01)
*A01H 5/04* (2018.01)
*A01H 6/74* (2018.01)

(52) U.S. Cl.
USPC ..... Plt./103
CPC ..... *A01H 6/749* (2018.05); *A01H 5/02* (2013.01); *A01H 5/04* (2013.01)

(58) Field of Classification Search
USPC ..... Plt./103, 133, 144
CPC . A01H 5/02; A01H 5/00; A01H 6/749; A01H 6/74
See application file for complete search history.

(56) References Cited

U.S. PATENT DOCUMENTS

PP32,531 P2 * 12/2020 Austin ..... A01H 5/02 Plt./103

* cited by examiner

*Primary Examiner* — June Hwu
(74) *Attorney, Agent, or Firm* — KPPB LLP

(57) ABSTRACT

A variety of rose plant of the shrub class, named 'AUSCP18729'. The 'AUSCP18729' is a variety of a rose with large, white blooms and many petals, with a light fragrance.

1 Drawing Sheet

Classification: The present invention relates to a new *Rosa hybrida* shrub of the market class 'English Rose'.

Variety denomination: The new plant has the varietal denomination 'AUSCP18729'.

ORIGIN OF INVENTION

This invention relates to a new and distinct variety of shrub rose plant named 'AUSCP18729', which was originated from the cross-pollination of the two 'unnamed' and unpatented seedlings of *Rosa hybrida.*

BACKGROUND OF THE INVENTION

The primary objective of this breeding was to produce a cut rose variety with large, white blooms and many petals, with a light fragrance.

SUMMARY OF THE INVENTION

Among the features which distinguish the new variety from others presently available and commercial rose cultivars known to the inventor is the following combination of characteristics: many petalled, large round, white blooms, with strong stems and a light fragrance, and a growth habit suitable for cut rose production.

Asexual reproduction of the new variety by cuttings as performed in Albrighton, United Kingdom shows that the foregoing and other distinguishing characteristics come true to form and are established and transmitted through succeeding asexual propagations. The cuttings successfully occurred on an unpatented plant/rootstock for the observed plants.

COMPARISON WITH PARENTS

The maternal and paternal parents of 'AUSCP18729' are two unnamed seedlings. The new rose may be distinguished from its seed parent, by the following combination of characteristics: the seed parent is pink in color with a hybrid tea bloom form, compared to 'AUSCP18729', which is white in color with flatter, rounder blooms. The new rose may be distinguished from its pollen parent, by the following combination of characteristics: the pollen parent has an apricot-pink color rather than white. The pollen parent also has a much shorter vase life when cut from the plant, when directly compared to 'AUSCP18729'.

COMPARISON WITH THE CLOSEST COMMERCIALLY AVAILABLE CULTIVAR

The most similar rose variety is 'AUSwagsy' (U.S. Plant Pat. No. 32,531). 'AUSwagsy' has few prickles on the stems, whereas 'AUSCP18729' has a medium amount of prickles. 'AUSwagsy' also has fewer petals (approx. 105), compared to 'AUSCP18729' (approx. 150). The glossiness of the upper side of the leaf is also different, with 'AUSwagsy' exhibiting a strong degree of glossiness and 'AUSCP18729' having a weak degree of glossiness. Finally, the fragrance of 'AUSwagsy' is stronger-of medium strength-as opposed to the very weak fragrance of 'AUSCP18729'.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

The top row of the accompanying photograph from left to right shows the lower surface of mature leaves, upper surface of mature leaves, and upper surface of immature leaves.

The second row of the accompanying photograph from left to right shows the reverse view of a half-open bloom and the reverse view of a fully open bloom.

The third row of the accompanying photograph from left to right shows the observe view of a half-open bloom and the observe view of a fully open bloom.

The left two and farthest right buds of bottom row of the accompanying photograph show flower buds at different stages of growth. The two buds with the black square backgrounds in the bottom row of the accompanying photograph show a flower with the petals removed to expose the pistils and stamens (left) and a flower with the petals and stamens removed to expose the pistils (right).

The outermost sides of the accompanying photograph show a mature stem with foliage removed (left) and an immature stem with foliage removed (right).

Throughout this specification, color references and/or values are based upon The Colour Chart of The Royal Horticultural Society (2001) except where common terms of color definition are employed.

DESCRIPTION OF THE NEW VARIETY

Observations of 'AUSCP18729' specimens were made in a greenhouse in Albrighton, Wolverhampton, United Kingdom. The following description is of three-year-old rose plants of the new variety grown in a garden environment in Albrighton, United Kingdom in the month of May. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 3.2 cm long and 2.3 cm in diameter when the petals start to unfurl.

*Form*.—The bud form is long pointed ovoid.

*Color*.—When sepals first divide, the bud color is RHS 150C (yellow-green group) with streaks of RHS60B (red-purple group). When half blown, the upper sides of the petals are RHS 157D (green-white group) and the lower sides of the petals are RHS 157D (green-white group).

*Calyx*.—Shape: star shape, with the sepals folding back against the stems. Diameter: 8.8 cm.

*Sepals*.—Arrangement: Regular. Color: Upper Surface: RHS 147D (yellow-green group). Lower Surface: RHS 144B (yellow-green group). Length: 3.6 cm. Width: 0.8 cm. Shape: Lanceolate. Apex: Overall shape, caudate. Margin: Smooth and slightly hairy. Surface texture: Upper Surface: Smooth, hairy. Lower Surface: Smooth. Number: There are 3 lightly appendaged sepals with smooth hairy edges.

*Receptacles*.—Color: RHS 143C (green group). Shape: Pitcher/cup. Size: Large, broad, long, about 1.1 cm long×1.4 cm wide. Surface: Smooth.

*Peduncle*.—Length: Medium, averaging about 6.15 cm. Surface: Smooth. Color: RHS 144B (yellow-green group). Strength: Strong.

Blooms:

*Type*.—Round.

*Size*.—Large, average open diameter is about 12 cm and average depth is about 3.5 cm.

*Borne*.—Singly. Other blooms nipped out for single bloom cut rose production. Number of flowers per stem was not observed for 'AUSCP18729' given its intended use as a cut flower.

*Form*.—When first open, bloom is globular. Permanence of bloom flattens: outer petal edges curl slightly.

*Upper profile*.—Flat.

*Lower profile*.—Flat.

Petalage: Number of petals under normal conditions: 150.

*Color*.—The upper sides of the petals are RHS 155A (white group). The reverse sides of the petals are RHS 155A (white group). The base of the petals has a very small basal spot on the upper and lower petal surfaces of RHS 5C (yellow group).

*Variegations*.—None.

*Discoloration*.—The general tonality at the end of the first day is RHS 11B (yellow group), and at the end of the third day is RHS 155A (white group).

*Fragrance*.—Slight. Character of fragrance: Myrrh.

Petals:

*Texture*.—Smooth, satiny and thin.

*Size*.—Width: 3.4 cm. Length: 4.8 cm.

*Surface*.—Smooth on the upper and lower surfaces of the petals.

*Shape*.—Broad elliptic outer petals, narrow elliptic inner petals.

*Margin*.—Entire.

*Apex shape*.—Rounded.

*Base shape*.—Rounded.

*Form*.—Incurve with some tips slightly recurved.

*Arrangement*.—Regularly arranged.

*Petaloids*.—Number: Approximately 5-10. Color: RHS 155A (white group). Length: 1.5 cm. Width: 0.8 cm. Shape: Obovate. Margin: Irregular.

*Persistence*.—Petals hang on and dry.

*Lastingness*.—On the plant: not tested. As a cut flower: long, approximately 10 days.

Reproductive parts:

*Stamens*.—Number: approximately 10. Length: approximately 0.55 cm.

*Anthers*.—Length: approximately 0.25 cm. Color: RHS 12B (yellow group). Arrangement: Regular around styles

*Filaments*.—Color: RHS 10A (yellow group). Length: 0.3 cm.

*Pollen*.—Color: RHS 5C (yellow group). Amount: Scarce.

*Pistils*.—Number: approximately 70. Length: approximately 0.9 cm.

*Styles*.—Color: RHS 155C (white group). Length: 0.8 cm.

*Stigmas*.—Color: RHS 63B (red-purple group). Length: 0.1 cm.

*Hips*.—NONE Observed as of the date of these observations.

PLANT CHARACTERISTICS

Plant form: Shrub.
Plant growth: Vigorous, upright.
Age to maturity: 2 years.
Mature plant: Height: 120 cm. Width: 70 cm.
Rootstock: Formed of 'AUSCP18729's' own root from the production of the cuttings for the observed plants in the United Kingdom.
Foliage:
*Number*.—Leaflets on normal mid-stem leaves is: 3 at the top of the plant, 5 further down (including terminal leaflet).
*Size*.—Medium, about 15 cm long×13 cm wide.
*Quantity*.—Normal. Number of leaves per flowering stem is: approximately 7-9.
*Color*.—New foliage: Upper side: RHS 144A (yellow-green group) with a perimeter of RHS 59B (red-purple group). Lower side: RHS 60A (red-purple group). Old foliage: Upper side: RHS 137A (green group). Lower side: RHS 138B (green group).
*Glossiness*.—Weak.
Leaflets:
*Size*.—About 7 cm long×4.5 cm wide.
*Shape*.—Pointed oval.
*Base shape*.—Rounded.
*Apex shape*.—Acuminate.
*Texture*.—Upper side: Leathery, smooth. Lower side: Leathery, smooth.
*Edge*.—Serrated.
*Serrations*.—Double/Large.
*Petiole*.—Color: RHS 144A (yellow-green group). Length: 4.5 cm. Width: 0.17 cm. Surface Texture: Smooth with prickles on underside.
*Petiole rachis*.—Color: upper side RHS 144A (yellow-green group). Underside: smooth with prickles. Lower Surface: smooth.
*Stipules*.—Length: 2 cm. Shape: Lateral. Descriptor: serrated/glandular. Apex: Acute. Color: RHS 143C (green group).
*Auricle*.—Shape: Lanceolate. Length: 1 cm. Width: 0.14 cm. Color: RHS 143A (green group).
*Vein color*.—RHS 137A (green group).
*Venation pattern*.—Reticulate.
*Margin*.—Margin undulation is medium.
Wood:
*New wood*.—Color: RHS 144A (yellow-green group) with flashes of RHS 185B (greyed-purple group). Bark: Smooth.
*Old wood*.—Color: RHS 143B (green group). Bark: Smooth.
Branching habit:
*Number*.—None-nipped for single cut rose production.
*Dimensions*.—Length: N/A. Diameter: N/A.
Stems:
*Mature stem*.—Length: approximately 100 cm. Diameter: 1.3 cm.
*Internode distance*.—approximately 5.25 cm. The above measurements are all variable, depending on growing conditions in a season.
*Stem pubescence present*.—No.
Prickles:
*Quantity*.—On main canes from base: ordinary. Number per stem length: 23 per 20 cm. On laterals from main canes: N/A.
*Form*.—Deep concave, some slender and slightly curved downward.
*Length*.—0.9 cm long×0.4 cm wide.
*Color when young*.—RHS 60A (red-purple group) with touches of light green (too small to get a color reading).
*Color when mature*.—RHS 177B (greyed-orange group).
Small prickles:
*Quantity*.—Main stalk: None. Number per stem length: N/A. Laterals: N/A. Number per stem length: N/A.
*Color*.—When young: N/A. When mature: N/A.
Anthocyanin coloration:
*Intensity*.—Anthocyanin coloration on the young shoot is weak.
Disease resistance:
*Powdery mildew* (*Podosphaera pannosa*).—Resistant.
*Downy mildew* (*Peronospora species*).—Resistant.
*Blackspot* (*Diplocarpon rosae*).—Resistant.
*Rust* (*Phragmidium tuberculatum*).—Resistant.
Pest Resistance: Not tested.
Winter Hardiness: Not tested.
Growing conditions: Normal greenhouse conditions.

What is claimed is;:

1. A new and distinct variety of English rose plant of the shrub class, named 'AUSCP18729', substantially as herein shown and described.

* * * * *

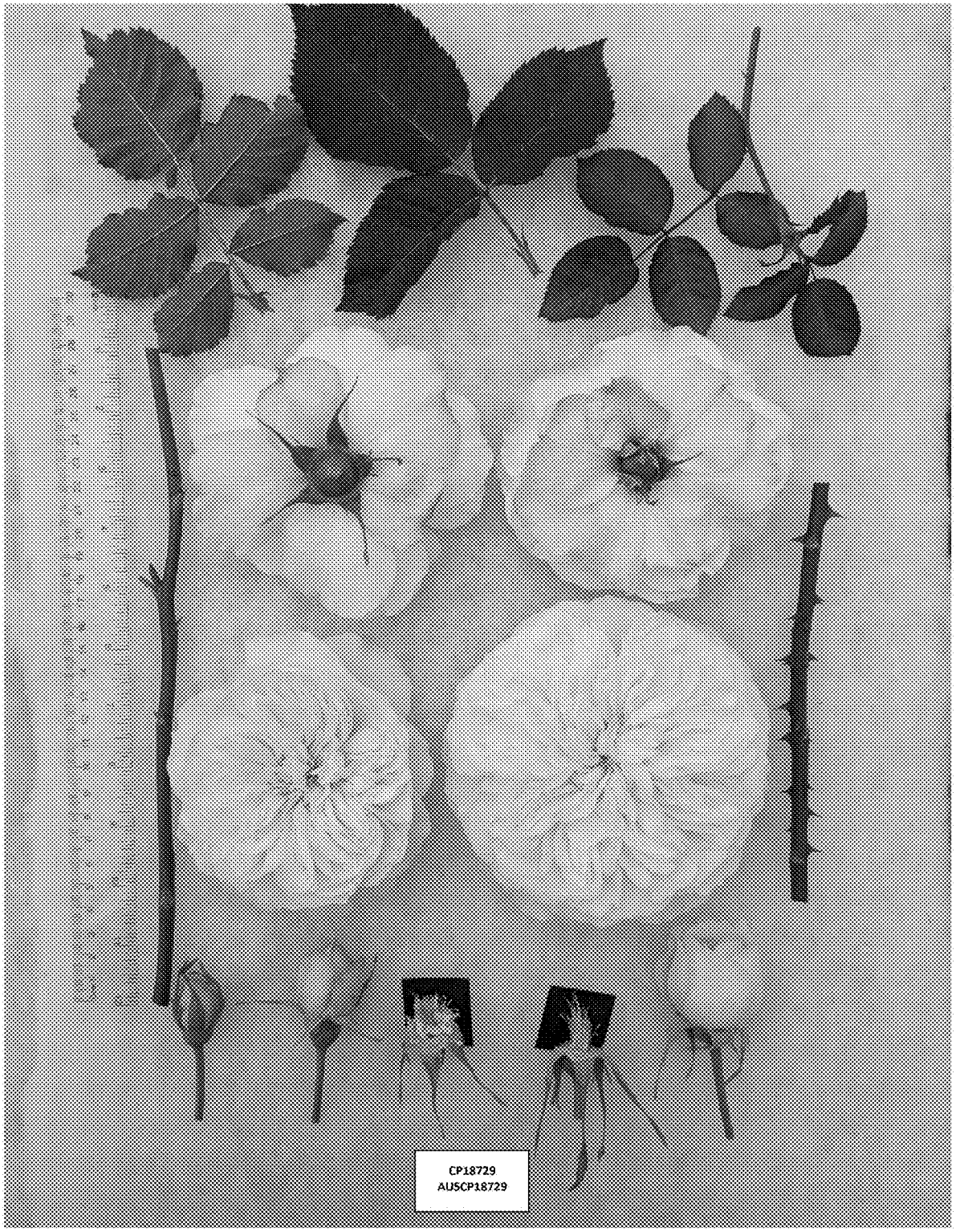
CP18729
AUSCP18729